United States Patent [19]

Tin

[11] Patent Number: 5,008,109
[45] Date of Patent: Apr. 16, 1991

[54] VESICLE STABILIZATION
[75] Inventor: George W. Tin, Arcadia, Calif.
[73] Assignee: Vestar, Inc., San Dimas, Calif.
[21] Appl. No.: 257,155
[22] Filed: Oct. 11, 1988

Related U.S. Application Data

[63] Continuation of Ser. No. 63,780, Jun. 18, 1987, abandoned, which is a continuation of Ser. No. 815,773, Jan. 2, 1986, abandoned, which is a continuation of Ser. No. 614,255, May 25, 1984, abandoned.
[51] Int. Cl.$^5$ ...................... A61F 13/00; A61K 9/127; A61K 47/36; A61K 47/42
[52] U.S. Cl. ..................................... 424/422; 264/4.1; 264/4.3; 424/1.1; 424/450; 424/484; 424/485; 424/488; 428/402.2; 436/829; 514/937; 514/944; 514/963; 514/965
[58] Field of Search .................. 264/4.1, 4.3; 428/402.2; 424/418, 450, 484, 488, 485, 422; 436/829; 514/944, 963, 965, 937

[56] References Cited

U.S. PATENT DOCUMENTS

| | | | |
|---|---|---|---|
| 3,527,712 | 9/1970 | Renn et al. | 252/315.3 X |
| 3,619,842 | 11/1971 | Maierson | 428/402.2 X |
| 4,185,618 | 1/1980 | Corey | 514/944 X |
| 4,217,344 | 8/1980 | Vanlerberghe et al. | 264/4.1 X |
| 4,235,871 | 11/1980 | Papahadjopoulos et al. | 264/4.6 X |
| 4,310,506 | 1/1982 | Baldeschwieler et al. | 264/4.1 X |
| 4,439,488 | 3/1984 | Trimnell et al. | 424/418 X |
| 4,493,894 | 1/1985 | Miyashiro et al. | 435/101 X |

FOREIGN PATENT DOCUMENTS

| | | |
|---|---|---|
| 0069307 | 6/1982 | European Pat. Off. . |
| 0160266 | 4/1984 | European Pat. Off. . |
| 8311716 | 7/1983 | France . |
| 8503640 | 8/1985 | PCT Int'l Appl. . |

OTHER PUBLICATIONS

"Carbopol Scales Up", Chemistry and Engineering News, 36, 64 & 65, Sep. 29, 1958.
The United States Pharmacopoeia-National Formulary Monograph, 1985, p. 1542.
Mauk et al., "Preparation of Lipid Vesicles Containing High Levels of Entrapped Radioactive Cations", Analytical Biochemistry, vol. 94, pp. 302-307, (1979).
Mauk et al., "Stability of Lipid Vesicles in Tissues of the Mouse", Proc. Natl. Acad. Sci. U.S.A., vol. 76, No. 2, pp. 765-769, (1979).
Frokjaer et al., "Stability and Storage of Liposomes", in Optimization of Drug Delivery, Alfred Benzon Symposium, 17, Bundgaard et al., Eds., Munksgaard, Copenhagen, pp. 384-397, (1982).
Weinstein et al., "Liposomes and Local Hyperthermia", Science, vol. 204, pp. 188-191, (1979).
Sheetz et al., "Effect of Sonication on the Structure of Lecithin Bilayers", Biochemistry, vol. 11, No. 24, pp. 4573-4581, (1972).
Lawaczeck et al., "The Formation and Annealing of Structural Defects in Lipid Bilayer Vesicles", Biochimica et Biophysica Acta, vol. 443, pp. 313-330, (1976).
Schullery et al., "Fusion of Dipalmitoyl Phosphatidylcholine Vesicles", Biochemistry, vol. 19, pp. 3919-3923, (1980).
Abra et al., "Liposome Disposition in Vivo", Biochimica et Biophysica Acta, vol. 666, pp. 493-503, (1981).
Kao et al., "Interactions of Liposomes with the Reticuloendothelial System", Biochimica et Biophysica Acta, vol. 677, pp. 453-461, (1981).
Ryman et al., "Potential Applications of Liposomes to Therapy", Annals N.Y. Acad. Sci., vol. 308, pp. 281-307, (1978).
Fendler, "Surfactant Vesicles as Membrane Mimetic Agents", Acc. Chem. Res., vol. 13, pp. 7-13, (1980).
Chemical Abstracts No. 188 156K (vol. 97, No. 22, Nov. 29, 1982).
Chemical Abstracts No. 187329V, (vol. 94, No. 23, Jun. 8, 1981).

Primary Examiner—Richard D. Lovering
Attorney, Agent, or Firm—Lyon & Lyon

[57] ABSTRACT

The present invention relates to a process of stabilizing micellular particles such as vesicles and increasing the shelf life by suspending the particles in a polymeric gel matrix. The invention also relates to such particles suspended in the gel matrix with a protective gel surface thereabout which is capable of becoming fluid and converting the protective surface of an aqueous suspension.

12 Claims, 1 Drawing Sheet

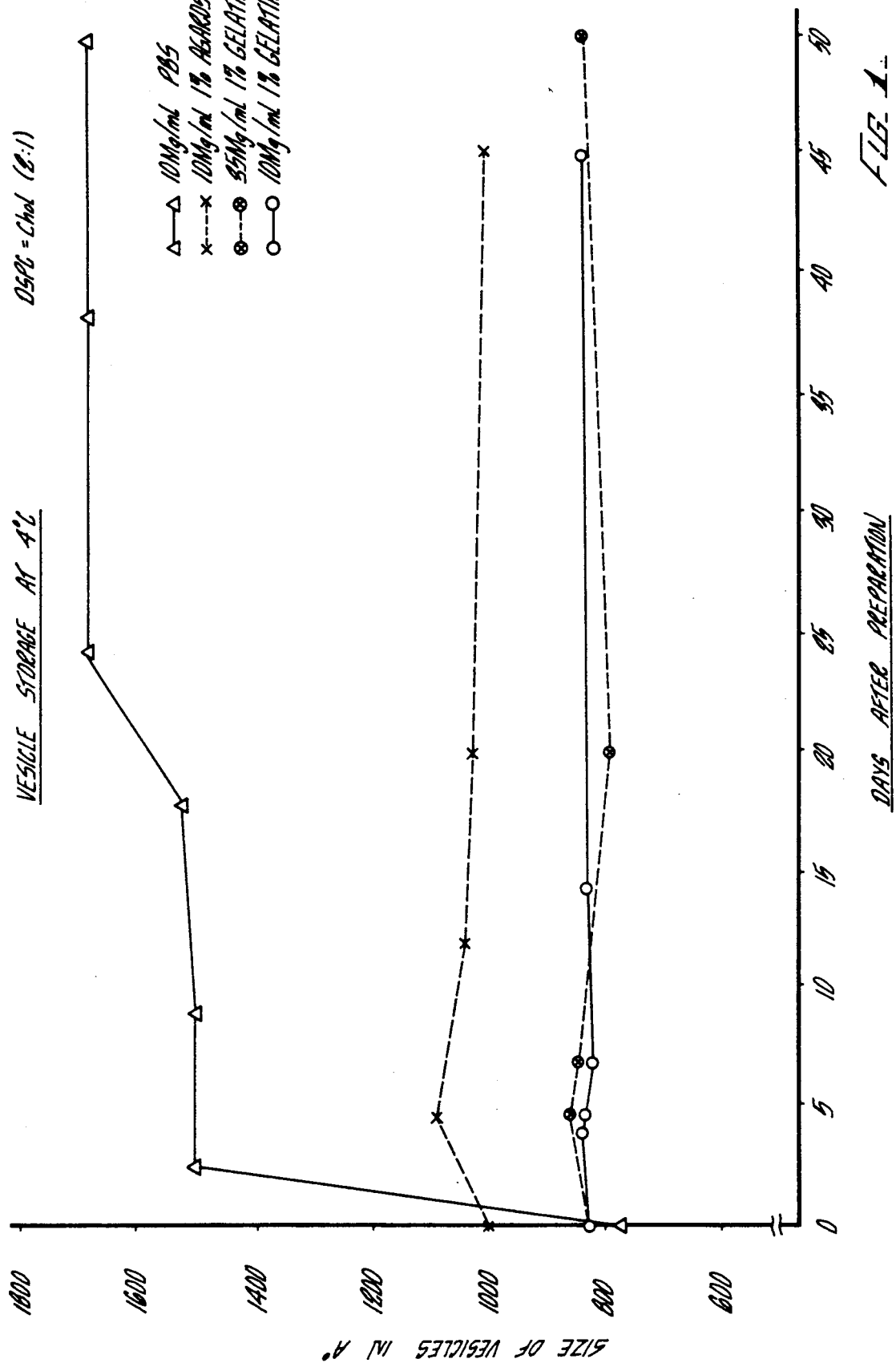

VESICLE STABILIZATION

This application is a continuation of application Ser. No. 063,780, filed June 18, 1987, now abandoned, which application is a continuation of application Ser. No. 815,773, filed Jan. 2, 1986, now abandoned, which application is a continuation of Ser. No. 614,255, filed May 25, 1984, now abandoned.

BACKGROUND OF THE INVENTION

1. Field of the Invention

The present invention relates to vesicle stabilization, and more particularly to such stabilization by suspending micellular particles such as vesicles in a polymeric gel matrix.

2. Description of Prior Art

The use of micellular particles such as phospholipid vesicles (or liposomes as they are commonly referred to) as carriers for pharmaceutical and diagnostic agents has been the subject of extensive investigation, Ryman B.E., et al., Ann. N.Y. Acad. Sci., 308, 281 (1978); Gregoriadis, G., Ed., "Liposome Technology", CRC Press, Inc., Boca Raton, Fla., Vol. II (1984); Fendler J.H., Acc. Chem. Res., 13, 7 (1980); and Weinstein J.N., et al., Science, 204, 188 (1979). Examples of the potential application of phospholipid vesicles include consideration as carriers of enzymes, drugs (particularly antitumor drugs), chelating agents, hormones, radionuclides, cell-modifying substances, antigens, antibodies, interferon inducers, and virus subunit particles. However, liposomes (especially small sonicated vesicles) are thermodynamically unstable at temperatures below the phase transition temperature, and tend to aggregate or fuse, to form larger unilamellar vesicles on long-term storage, Sheetz M.P., et al., Biochemistry, 11, 4573 (1972); Lawaczeck R.L., et al., Biochem, Biophys. Acta, 443, 313 (1976); Larrabee H.L., Biochemistry, 18, 3321 (1978); and Shullery S.E., et al., Biochemistry, 19, 3919 (1980).

Aggregation or fusion of the small particles into larger particles alters the properties of the vesicles, which can in turn modify the permeability of the vesicles and in vivo biodistribution, Kao Y.J., et al., Biochem. Biophys. Acta., 677, 453 (1981); and Abra R.M., et al., Biochem. Biophys. Acta., 666, 493 (1981). It is accordingly highly important to be able to store micellular particles without having the particles aggregate or fuse together with the resultant potential change in important properties.

SUMMARY OF THE INVENTION

According to the present invention, the foregoing aggregation or fusion is overcome by the storage of micellular particles in a polymeric gel matrix. The matrix may be a natural or synthetic matrix that will gel at low temperatures and capable of becoming fluid, as by melting at room temperature or a higher temperature. Examples of suitable such materials are polysaccharides and polypeptides. Upon storage at colder temperatures, the gel solidifies and restricts the motion of the particles. In turn, this slows down or prevents aggregation or fusion.

Thus, the size and properties of the micellular particles remain the same size throughout storage and as long as the gel remains in its solidified state. However, at room temperature or higher, the gel will melt and the vesicle or other particle will return to its original form as a suspension in an aqueous medium which can be used for injection or other application in the same manner as freshly prepared vesicles, without alteration of significant properties or in vivo biodistribution.

Examples of vesicles to which the present invention is applicable are phospholipids such as distearoylphosphatidylcholine (DSPC), dipalmitoylphosphatidylcholine (DPPC), and dimyristoylphosphatidylcholine (DMPC) and natural phospholipids such as egg lecithin and soybean lecithin. The vesicles may also have enclosed therein a therapeutic agent such as an antibiotic and, as will be shown from the illustrative examples which follow, the vesicles may be labelled after storage with a radionuclide such as $^{111}$In.

DETAILED DESCRIPTION OF THE INVENTION

Definitions and Abbreviations

As used herein, "micellular particles" and "micelles" refer to particles resulting from aggregations of amphiphillic molecules, with preferred amphiphiles being biological lipids.

"Vesicle" refers to a micelle in a generally sperical form, often obtained from a lipid which forms a bilayered membrane and is referred to as a "liposome". Methods for forming such vesicles are well known in the art; typically, the vesicles are prepared from a phospholipid, for example, distearoylphosphatidylcholine or lecithin, and may include other materials such as neutral lipids and surface modifiers such as positively or negatively charged compounds, antigens, antibodies, saccharides and lectins. Depending on the techniques for preparation, the vesicle may be a simple bilayered spherical shell (a unilamellar vesicle) or may have multiple layers (multilamellar vesicles).

DSPC—distearoylphosphatidylcholine
Chol—cholesterol
DPPC—dipalmitoylphosphatidycholine
DMPC—dimyristoylphosphatidylcholine
DTPA—diethylenetriaminepentaacetic acid
EDTA—ethylenediminetetraacetic acid
SUV—small unilamellar vesicles

Material and Method of Preparation of Micelles

L-γ-distearoylphosphatidylcholine (DSPC) from Calbiochem and cholesterol (Chol) from Sigma were used without further purification. Cholesterol oleate [Oleate-1-$^{14}$C] (Specific activity 51 Ci/mole) and $^{14}$C-ethylenediamine tetraacetic acid [Acetic 2-$^{14}$C] (EDTA; specific activity 4.38 mCi/mmole) were purchased from New England Nuclear. Sodium salt of nitrilotriacetic acid (NTA) and EDTA were purchased from Baker Chemical Company. Radiochemical $^{111}$InCl$_3$ (research grade) was purchased from Medi-Physic and used without purification. Ionophone A23187 was purchased from Calbiochem. Agarose (Type IX) was obtained from Sigma and gelatin (Knox gelatin) was purchased commercially. Agarose is the neutral gelling fraction of the polysaccharide complex, Agar, extracted from the agarocytes of algae of the Rhodophycae, while gelatin is a heterogenous mixture of water soluble, high molecular weight proteins derived from collagen. BDF1 mice were obtained from Simonson Laboratories (Gilroy, Calif.).

Preparation and Loading of Vesicles

Small unilamellar vesicles were prepared and loaded according to the method of Mauk and colleagues, Mauk M.R. & Gamble R.C., Proc. Natl. Acad. Sci USA, 76, 765 (1979). Briefly, a lipid mixture was prepared by mixing DSPC, Chol, and A23187 in the molar ratio of 2:1:0.004. The lipid mixture was dried on the vaccum overnight and then sonicated in phosphate-buffered saline (PBS, pH 7.4) containing 1 mM NTA or as otherwise specified. $^{14}C$ - or $^{3}H$ cholesterol oleate was included as a marker for the lipid phase. After sonication, annealing and low speed centrifugation, the vesicles were separated from excess NTA by passing over a Sephadex G-50 column equilibrated with PBS.

Vesicles were loaded with $^{111}InCl_3$ by adding the radionuclide to the vesicle preparation and incubating at 80° C. for 45 minutes. After incubation, excess EDTA was added to complex with free $^{111}In$ on the surface of the vesicle or in the solution. These free $^{111}In$-EDTA complex were then separated from loaded vesicles by column chromatography using Sephadex G-50.

Dynamic Light Scattering Measurements

Vesicle size is measured by dynamic light scattering which is concerned with the time behavior of the fluctuations in the scattering intensity, Frokjaer S., et al., Alfred Benzon Symp., 17, 384 (1982). As the particles undergo continuous Brownian motion, the scattering intensity undergoes a large fluctuation from zero (total destructive interference) to a maximum value (no interference). The diffusion coefficient of the diffusing particles is related to the mean life time of the fluctuation in the intensity of the scattering light. Generally, the larger the particles, the slower the diffusion and the longer the mean life time of the fluctuation. For spherical particles (such as liposomes), the diffusion coefficient (D) is related to the hydrodynamic radius ($r_h$) by the Stokes-Einstein relation: $D - k_B T/6 r_h$ where $k_b$ is the Boltzmann constant, T is the absolute temperature and is the viscosity of the solvent.

A dilute sample of vesicle suspension in filtered PBS were prepared in clean 6×50 mm test tubes. The light scattering measurement was made with a NiComp model TC-200 computing-autocorrelator particle sizer. The instrument is equipped with a 64 channel 4-bit autocorrelator and a 5 mW low noise He-Ne laser.

EXAMPLE I

Small unilamellar vesicles (SUV) composed of DSPC and Chol in the molar ratio of 2 to 1 were prepared according to the method described. $^{14}C$-Cholesterol Oleate was included as the lipid marker. After sonication, annealing and low speed centrifugation, the vesicles were mixed with either gelatin or agarose in a sterilized vial to a final concentration of (1) 10 mg of SUV per ml of 1% gelatin solution; (2) 35 mg of SUV per ml of 1% gelatin solution; or (3) 10 mg of SUV per ml of 1% agarose solution. All the vials were then stored in a refrigerator at 4° C. At different times after preparation, samples of vesicle at different concentration or polymeric medium were melted at room temperature. Dilute samples of these vesicles in PBS were prepared and the size was measured by laser light scattering as described in the method section. As shown in FIG. 1, the size remained unchanged when the vesicles were stored in either the gelatin or agarose matrix. On the other hand, the vesicles in PBS aggregated or fused within a short period of time after preparation.

EXAMPLE II

In the previous example, it is shown that the size of the vesicle in a polymeric matrix remains unchanged for a prolonged period of time. However, it is also very important in a pharmaceutical context that the liposome retain the entrapped material within the vesicle for a reasonable shelf-life. This example shows no leakage of entrapped material in vesicle in a 1% gelatin medium at 4° C.

1 mM $^{14}C$-EDTA in PBS was sonicated with DSPC and Chol (2:1) which was labeled with a trace amount of H-cholesterol Oleate. The free unencapsulated EDTA was separated from the entrapped material by passing through a Sephadex G-50 column. The $^{14}C$-EDTA encapsulated SUV's were then mixed with gelatin to a final concentration of 10 mg/ml of 1% gelatin solution and stored at 4° C. The leakage of entrapped EDTA as a function of time can be monitored by the decrease in the ratio of $^{14}C$ to $^{3}H$. As shown in table I, not only the size of vesicle remains unchanged, but the material inside the vesicle structure also remains entrapped throughout the storage.

TABLE I

| Stabilization effect of gelatin on size and encapsulated material in vesicle | | |
|---|---|---|
| Days after Preparation | Size A° | $^{14}C/^{3}H$ |
| 0 | 867 | 0.143 |
| 3 | 888 | 0.154 |
| 7 | 888 | 0.147 |
| 9 | 880 | 0.157 |
| 43 | 881 | 0.157 |

EXAMPLE III

To further illustrate the physical properties of vesicles after storage, vesicles stored in gel matrix were loaded with radioactive $^{111}In$. A gamma-ray perturbed angular coincidence spectrometer (PAC) was used to measure the intactness of vesicles after loading, Kwang K.J. & Mauk M.R., Proc. Nat'l. Acad. Sci. USA., 74, 4991 (1977); and Meares C.F. & Westmoreland D.G., Cold Spring Harbor Symp. Quart. Biol., 36, 511 (1971). The spectrometer measures the rotational correlation time of $^{111}In$ in which the correlation time is related to the tumbling rate of the radionuclide. When the $^{111}In$ is encapsulated within the vesicles, it exhibits a high tumbling rate (high $G_{22}$) because of its binding to the small chelator within the vesicle. However, once the vesicle is disrupted (such as disruption by addition of isopropanol) or the entrapped material leaks out of the vesicle by other means, it binds to any surrounding protein present which markedly decreases the tumbling rate. In the following, it is apparent that 1 and 20 day old DSPC and Chol (2:1) vesicles stored in 1% gel at 4° C have properties comparable to freshly prepared vesicles after loading. The $G_{22}$ remains the same with and without serum indicating the long term storage has no damaging effect on the membrane of the vesicles.

TABLE II

| | $(G_{22})$ | | |
|---|---|---|---|
| | 1 day old vesicle stored in 1% gel at 4° C. | 20 day old vesicle stored in 1% gel at 4° C. | freshly prepared vesicles |
| Vesicle + PBS | 0.44 | 0.46 | 0.45 |
| Vesicle + serum | 0.48 | 0.46 | 0.44 |
| Vesicle + serum + isopropanol | 0.1 | 0.06 | 0.09 |

EXAMPLE IV

Finally, to stress the importance of maintaining the size of vesicle, the biodistribution of these aged vesicles in tumor mice was studied. DSPC, Chol (2:1) vesicles encapsulated with 1 mM NTA were stored in a 1% gelatin solution at 4° C. At specific time after preparation, the gel matrix was melted at room temperature. The vesicles suspended in this aqueous solution were then loaded as previously described. After loading, 1 mg of the loaded vesicles were injected intravenously in BDF1 mice with a 6–8 day old Lewis Lung Carcinoma. The mice were then sacrificed at 24 hrs after injection. By gamma counting, the biodistribution of the injected vesicles was calculated as the amount of radioactivity per gram of tissue. The biodistribution of these aged vesicles were compared with the biodistribution of the freshly prepared vesicle in the same strain of mouse. No significant difference (Student t test, p 0.001) was found between freshly prepared vesicle and vesicle in gelatin, as is set forth in TABLE III.

TABLE III

Biodistribution of In-NTA encapsulated vesicle in tumor mice.

| Days After Preparation | % Injected dose/gm tissue | | | | |
|---|---|---|---|---|---|
| | Tumor | Lung | Liver | Spleen | Kidney |
| 0 (without gelatin) | 19.62 ± 4.41 | 14.01 ± 2.81 | 31.38 ± 5.58 | 15.52 ± 5.67 | 14.78 ± 0.41 |
| 7 | 21.58 ± 2.57 | 16.31 ± 3.36 | 36.77 ± 6.06 | 19.32 ± 1.52 | 15.67 ± 2.24 |
| 28 | 27.62 ± 2.04 | 14.36 ± 6.82 | 34.56 ± 2.13 | 21.88 ± 2.57 | 13.88 ± 0.55 |
| 50 | 23.17 ± 5.09 | 17.25 ± 4.47 | 32.72 ± 1.63 | 23.35 ± 1.64 | 14.29 ± 0.64 |

Suitable for use as the gel matrix in the present invention are any of a number of polymeric materials, including natural and synthetic materials. Examples are polysaccharides, such as gum arabic, ethyl cellulose, hydroxylated starch and Kelgin, polypeptides, and polyesters synthesized from lactide or acid, poly ($\beta$-hydroxybutyrate), poly(DL-lactide-co-glycolide). As used in the foregoing examples, agarose is illustrative of suitable polysaccharides, while gelatin is illustrative of suitable polypeptides. It will be understood by those skilled in the art, that other polymeric gel materials can be utilized within the confines of the present invention, as long as the particular such material is capable of forming the desired protective gel surface around the micellular particles at low temperatures and being transformed to a fluid, for example, by melting at approximately room temperature or higher, to become an aqueous suspension. While the use of a gel matrix capable of such transformtion by melting is preferred, it will be appreciated that such materials capable of the indicated transformation by other means, e.g., enzymatic, may also be utilized.

It will be also understood that while the percentage of gel in the solution or matrix is less significant to achieving the desired stabilization of the particles, it is very important with respect to the temperature at which the gel matrix is formed. Thus, for example, utilizing a gel solution of approximately 1% gel content, solidification will occur at approximately 4° C., whereas with a 10% gel solution, solidification will occur at approximately room temperature. In view of such considerations, the gel matrix will typically be a solution of from about 0.5% by weight to about 10% by weight gel, with about 1–5% by weight being the preferred range.

As indicated previously, any of a variety of therapeutic agents may be enclosed in the micellular particles. Illustrative therapeutic agents include antibiotics, metabolic regulators, immune modulators, chemotherapeutic drugs, toxin antidotes, etc. By the same token, the particles may be loaded with 111In or other diagnostic radionuclide, e.g., other gamma emitters such as Ga-67, Tc-99M, Cr-51, I-125, etc, and fluorescent materials or other materials that are detectable in in vitro applications.

From the foregoing examples, it is clear that the present invention provides for the stabilization of micellular particles during storage for extended periods of time. By suspending the particles within a polymeric gel matrix to form a protective gel surface around the particles, aggregation or fusion of the particles is avoided without sacrifice of the utility of the vesicles or leakage of any enclosed material.

What is claimed is:

1. A method for the storage and use of small micellular particles, comprising the steps of: suspending said micellular particles in a pharmaceutically acceptable polymeric gel solution to form a suspension with a protective gel surface about said micellular particles; cooling the suspension to form a gel matrix which restricts movement of the particles; and warming the gel matrix to at least about room temperature, thereby transforming the gel matrix into an aqueous suspension suitable for use.

2. The method of claim 1 in which said gel matrix is a polysaccharide or polypeptide.

3. The method of claim 2 in which said polymeric gel matrix is a gelatin or agarose.

4. The method of claim 1 in which said micelluar particles are phospholipid vesicles.

5. The method of claim 4 in which said vesicles have a therapeutic agent enclosed therein.

6. The method of claim 1, 2 or 4 in which said gel matrix is a solution containing from about 0.5 to about 10% by weight gel.

7. The method of claim 6 in which said polymeric gel matrix contains from approximately 1 to about 5% by weight gel.

8. The method of claim 1 further comprising injecting the aqueous suspension in vivo after it has been transformed from a gel matrix to an aqueous suspension.

9. A method for the storage of micellular particles, comprising suspending said micellular particles in a pharmaceutically acceptable polymeric gel solution to form a suspension with a protective gel surface about said micellular particles, said suspension being fluid at room temperature, cooling said suspension to form a gel matrix which restricts movement of said particles, and subsequently warming the gel matrix to at least about room temperature to return the gel matrix to its fluid state.

10. The method of claim 9 in which said gel matrix is a polysaccharide or polypeptide.

11. The method of claim 10 in which said polymeric gel matrix is a gelatin or agarose.

12. The method of claim 9 in which said micellular particles are phospholipid vesicles.

* * * * *